(12) United States Patent
Vellinga et al.

(10) Patent No.: US 8,728,318 B2
(45) Date of Patent: May 20, 2014

(54) SETTLING DEVICE, PURIFIER COMPRISING A SETTLING DEVICE AND METHODS FOR ANAEROBIC OR AEROBIC PURIFICATION OF WASTE WATER

(75) Inventors: Sjoerd Hubertus Jozef Vellinga, Tjalleberd (NL); Antonius Johannes Jorna, Balk (NL)

(73) Assignee: Paques I.P.B.V., Balk (NL)

( * ) Notice: Subject to any disclaimer, the term of this patent is extended or adjusted under 35 U.S.C. 154(b) by 472 days.

(21) Appl. No.: 13/120,223

(22) PCT Filed: Sep. 23, 2009

(86) PCT No.: PCT/NL2009/050570
§ 371 (c)(1),
(2), (4) Date: Mar. 22, 2011

(87) PCT Pub. No.: WO2010/036107
PCT Pub. Date: Apr. 1, 2010

(65) Prior Publication Data
US 2011/0168021 A1    Jul. 14, 2011

(30) Foreign Application Priority Data
Sep. 23, 2008  (EP) ................................. 08164924

(51) Int. Cl.
*C02F 3/28* (2006.01)
*C02F 11/04* (2006.01)

(52) U.S. Cl.
USPC ........... 210/603; 210/608; 210/621; 210/188; 210/521

(58) Field of Classification Search
USPC ......... 210/603, 605, 608, 621, 513, 515, 521, 210/532.1, 188
See application file for complete search history.

(56) References Cited

U.S. PATENT DOCUMENTS

| 3,953,332 | A  | * | 4/1976 | Speth et al. ................... | 210/737 |
| 4,747,948 | A  | * | 5/1988 | North ........................... | 210/633 |
| 2002/0000409 | A1 | * | 1/2002 | Lanting et al. ............... | 210/603 |
| 2003/0046912 | A1 | * | 3/2003 | Vellinga ....................... | 55/444 |

FOREIGN PATENT DOCUMENTS

| EP | 0 193 999 A1 | 9/1986 |
| EP | 0 244 029 A1 | 11/1987 |
| EP | 0 820 335 B1 | 1/1998 |
| EP | 1 291 326 A2 | 3/2003 |

(Continued)

OTHER PUBLICATIONS

International Search Report, dated Dec. 28, 2009, from corresponding PCT application.

*Primary Examiner* — Fred Prince
(74) *Attorney, Agent, or Firm* — Young & Thompson

(57) ABSTRACT

A three phase separator or settling device (2) or a digester (1) including the settling device. The settling device can receive a fluid containing liquid, gas and particulate material. The settling device includes a settling chamber to be filled with this fluid. The device can also include a liquid-discharge (5) for discharging liquid from the settling chamber and fitted close to the liquid level (30), a fluid inlet (6) for supplying the fluid into the settling chamber (3), a particulate material separation device (7) and a sludge outlet (8). A flow of fluid is provided into and out of the settling device and settling chamber. The inlet includes a gas separation device (4) for separating gas from the fluid including channels, the inlet positioned close to the fluid level. The inlet and transition (75) into the settling chamber is arranged to create a pre-separated flow pattern including a generally laminar liquid flow.

20 Claims, 4 Drawing Sheets

(56) References Cited

FOREIGN PATENT DOCUMENTS

| | | | |
|---|---|---|---|
| GB | 1 585 141 A | | 2/1981 |
| JP | 5-337490 A | * | 12/1993 |
| JP | 10-328505 A | * | 12/1998 |
| WO | 92/01637 A1 | | 2/1992 |
| WO | 96/23735 A1 | | 8/1996 |
| WO | 96/32177 A1 | | 10/1996 |
| WO | 2006/137736 A2 | | 12/2006 |

* cited by examiner

__US 8,728,318 B2__

SETTLING DEVICE, PURIFIER COMPRISING A SETTLING DEVICE AND METHODS FOR ANAEROBIC OR AEROBIC PURIFICATION OF WASTE WATER

The invention concerns a settling device for a fluid containing liquid gas and particulate material. The invention also concerns a purifier comprising such a settling device. In a further embodiment the invention also concerns methods for aerobic or anaerobic purification of waste water.

Such settling devices are known from the prior art. An example is disclosed in EP 0 820 335 A1, incorporated by reference. Purifiers and settling devices can be used for aerobic or anaerobic purification of waste waters. The waste water comprises a fluid which can contain dissolved and non dissolved organic and/or anorganic material.

Anaerobic wastewater treatment is the biological treatment of wastewater without the use of air or elemental oxygen. Many applications are directed towards the removal of organic pollutants in waste water, slurries and sludges. The organic pollutants are converted by anaerobic micro organisms to a gas containing methane and carbon dioxide, known as "biogas"

In the waste water engineering field organic pollution is measured by the weight of oxygen it takes to oxidize it chemically. This weight of oxygen is referred to as the "chemical oxygen demand" (COD). COD is basically a measure of organic matter content or concentration. The best way to appreciate anaerobic wastewater treatment is to compare its COD balance with that of aerobic wastewater treatment.

In the anaerobic process methane could be a reaction product. Methane is a valuable fuel. Very little COD is converted to sludge (less than 10%). In an aerobic waste water treatment generally more than 50% is converted.

BACKGROUND

A majority of the existing plants use Upflow Anaerobic Sludge Blanket (UASB) or expanded granular sludge bed (EGSB).

The upflow anaerobic sludge blanket (UASB) process is a high-loaded process that generally employs a reactor containing a bed of granular anaerobic sludge. Influent wastewater is evenly distributed beneath the bed and flows upward through the biomass bed. The biomass/substrate contact is developed through the hydraulic flow distribution and biogas generation. A three-phase separator is employed at the top of the reactor to separate biogas and solids from the liquid. For proper operation the UASB process depends on the growth of granular or flocculated sludge.

Anaerobic expanded granular sludge bed (EGSB) technology is another technology applied in prior art arrangements. Sludge performance is critically dependent on the efficient distribution of the influent/recycle stream to ensure a rapid, uniform flow through the reactor bed and adequate biomass growth.

The settler device could be used in combinations of different techniques (hybrid reactor systems) such as anaerobic filters and/or anaerobic lagoons The invention relates to all applications in which a fluid contains gas and/or particulate material, and in which a three phase separator or hereinafter settler device is used to at least partially separate the two or three phases from that fluid.

An application of a purification process comprising a settler device according to the invention comprises a reactor. Examples are aerobic, anaerobic or anoxic reactors.

Anaerobic granular sludge bed technology refers to a reactor concept or purifier for the anaerobic treatment of wastewater.

A (UASB/EGSB/aerobic) reactor according to the invention comprises a tank having a fermentation chamber. Waste water is distributed into the tank, in an embodiment at appropriately spaced inlets. The waste water passes upwards through a(n anaerobic) sludge bed where the micro organisms in the sludge come into contact with waste water substrates. In an embodiment the resulting anaerobic degradation process in the fermentation chamber is responsible for the production of gas (e.g. biogas containing $CH_4$ and $CO_2$). The upward motion of released gas bubbles causes hydraulic turbulence that provides reactor mixing without any mechanical parts. The fluid is continuously in motion in the fermentation chamber due to gas flows that find their way upwards through the fluid towards the liquid level.

At the top of the reactor, the water phase is separated from sludge solids and gas in a three-phase separator (also known the gas-liquid-solids separator) or settling device. The three-phase-separator is commonly a gas cap with a settler situated above it. Below the opening of the gas cap, baffles can be used to deflect gas to the gas-cap opening.

A settling device comprises at least a settling chamber. Fluid from the process (e.g. fermentation) chamber can enter the settling device and settling chamber. Preferred circumstance for the settling chamber is a relatively low turbulence. The fact that the fluid present in the settling chamber is relatively still means that particles which are present in that fluid are able to settle, these particles being able to fall back to the process chamber. The settling device is constructed and arranged for the (further) separation of the gas and/or liquid and/or particulate elements in the fluid. A settling device discharge preferably contains cleaned fluid/liquid.

Invention

The primary object of the present invention is to provide a separation device in which a liquid, gas and particulate material can be separated, such that at an exit of the settling device a liquid is collected which is essentially free from particulate material and/or, preferably, essentially free from gas.

It is a goal of this invention to improve the circumstances for separation of particulate material from fluid in the settling device. It is a further goal to increase the efficiency of separation and/or the capacity per unit volume in respect of the prior art.

In an embodiment the settling device is provided for fluids containing liquid gas and particulate material (sludge). The settling device can comprise:
 a settling chamber configured to be filled with the fluid;
 a liquid-discharge for discharging liquid from the settling chamber, the liquid discharged being arranged so as to be fitted close to the liquid level, when in operation;
 a fluid inlet configured to supply the fluid into the settling chamber, and arranged essentially at the same level as the liquid-discharge;
 particulate material separation device and
 a sludge outlet for discharging fluid containing sludge.
In the settling device separation of the fluid is accomplished by providing one or more separation devices. A liquid-discharge is positioned downstream from the settling chamber. The liquid discharge is preferably a discharge for an effluent. The liquid can reach the discharge only after entering through the inlet, passing along the separation devices and the settling chamber.

The settling device is preferably mounted in a reactor. The inlet and sludge outlet are connected to the reactor. The sludge outlet is a return flow outlet, which in combination with the inlet allows a generally circulating flow of fluid. Driving force for this circulation can be a density difference in the fluid. Preferably the driving force of the flow is a density difference of the fluid outside the settler device containing more gas (lower density) than inside.

The inlet is preferably connected to a degassing compartment of a reactor. The flow that enters from the degassing compartment is the sum of the effluent flow and the sludge return flow. The effluent flow also passes through the settling compartment where the particles are separated from the fluid before the fluid is discharged (leaving the reactor.) The effluent flow can be controlled with the amount of inflow into the reactor.

The fluid can reach the settling chamber and particulate material can be separated from the liquid. The particulate material and part of the fluid can leave the settling chamber through a sludge outlet, the outlet bringing the dense material back into the process or fermentation chamber. Separation device such as particulate material separation device can be provided in order to further aid the separation.

In an embodiment according to the invention the inlet means comprises gas separation device for separating gas from the fluid. Since the inlet means comprise the gas separation device, and preferably the inlet means are formed by gas separation device, the amount of gas present in the settling chamber will be much lower causing little disturbance in further separation of the particulate material from the fluid. This will increase the efficiency of the settling device.

A gas separation device according to the invention comprises a device that is constructed and arranged to actively separate gas from the fluid. The gas separation device according to the invention will separate at least 50% of the gas present in the fluid from said fluid during passage of the fluid through the gas separation device. In a preferred embodiment at least 70%, and further preferred at least 90%, of the gas content is separated from the fluid.

If the inlet is connected to the degassing compartment and comprises the gas separating device according to the invention, floating sludge will not be allowed to enter the settling device/chamber.

It is known from prior art to provide a threshold for gas to enter the inlet/settling chamber. From EP 0 820 335, included by reference, it is known to provide a downward directed entrance toward the settling chamber. This however is not a separation device. It is not constructed and arranged to separate gas from the fluid.

A skilled person will not be inclined to position a separation device in the inlet as it will partially block the inflow of fluid into the settling chamber. However it was found surprisingly that the further gas separation function increases the efficiency of the settling device. The increased efficiency outweighs the friction loss.

In an embodiment the gas separation device comprises channels, preferably oblique (with respect to a vertical) channels. The prior art provides different embodiments of gas separation device comprising elongated channels. In oblique channels gas will collect at an upper side of the channel due to floating.

In a further embodiment the gas separation device comprises an inlet close to the fluid level and an outlet in the settling chamber at a lower level. The level difference will provide a threshold for gaseous fragments to reach the settling chamber. Bubbles in the fluid have a lower density and will tend to float. A gas separation device will in an embodiment comprise a downwardly directed partition.

In an embodiment the gas separation device comprises a row of oblique parallel plates. An oblique plate or tilted plate settling device or lamella settler allows separation of a fraction from a fluid. Fluid will be supplied at a top of the construction and will flow in a partially downward direction. A flow directed downwardly through such a plate structure, will result in gas collection near an underside of the higher plate, while particulate material will collect near an upper side of the lower plate between which a channel is formed. During the oblique flow, the gas bubbles present therein will rise, as a result of their climbing capacity, more steeply than other parts of the fluid and will finally come into contact with an underside of the obliquely placed plate. The accumulated gas bubbles collected at the under side of the plate will result in a slowing down of the (downwards) gas flow and will eventually cause a reversal in the flow direction of the gaseous part, back towards the inlet of the gas separator. The collecting of gas will result in a counter flow countering the downwardly directed fluid flow at an underside of the above higher plate. The gas will be discharged from the plate construction through the inlet at the same side where it entered.

The gas separation device according to a preferred embodiment will not only separate the gas bubbles but heavier particles will settle on the separator plates. The sludge collect on the lower plates. Due to frictional contact (sludge load; viz. kg sludge/h) the flow of the collected sludge over the settling plates is lower than the fluid flow between the plates.

The inclined plates of the separation device according to the invention will generally be fitted at an angle of 30° to 80° to the horizontal. In an embodiment, this angle will measure 55° to 65°. The value can depend upon the process conditions and the composition of the fluid to be treated. An angle of about 50° to 65°, such as, for example, an angle of about 55°, has been shown to produce good results under diverse process conditions and with respect to diverse compositions of the fluid to be treated.

A semi-laminar flow between the plates, in which particles present in the fluid can easily be settled, can be realized according to the invention where the plates are fitted in overlapping arrangement at mutual horizontal intervals of about 2-18 cm, preferably 4-12 cm, even more preferably 8-13 cm. Such plates, with a length of at least 50 cm, preferably 80 cm, and in a preferred embodiment at least 115 cm, are used in the preferred embodiment for gas separation. In an embodiment the plates are at most 200 cm long.

A semi laminar flow according to an aspect of the invention comprises a flow of the fluid which is close to a laminar flow of the liquid part of the fluid. The flow is not turbulent. Preferably the flow of the fluid into the settling device and preferably when the flow reaches the settling chamber is close to laminar. Hereinafter reference will be made to a semi-laminar flow which will refer to a combination of a generally laminar liquid flow and other flows, such as a sludge flows. These sludge flows can be laminar and can be at a similar speed or lower flow speed, e.g. due to the sludge load and/or sludge density.

In an embodiment fluid is first arriving at or almost at the water level of a tank, hereinafter the degassing compartment of the tank, the tank being equipped with a settling device according to the invention. Most of the gas is already released from the fluid before entering the settling device. The fluid is forced downward along an inclined plate of the gas separation device. Further downstream near an end of the oblique plates, solids continue their way downwards into the settling chamber. The settling chamber comprises a cavity in the settling device of suitable volume.

In a preferred embodiment the sludge particles are transferred back to the process chamber. A suitable outlet is positioned in the settling chamber allowing a flow out of the setting chamber. In a preferred embodiment a flow of sludge particles from the inlet of the settling device through the settling chamber is more or less an undisturbed flow.

In an embodiment a flow towards the liquid discharge device is provided in the settling chamber, wherein the flow towards the liquid discharge device is directed at least partially in an opposite direction with respect to the inlet flow from the inlet into the settling chamber. The inlet flow into the separation chamber is in this embodiment not directed towards the liquid discharge. This further hinders sludge particles to reach the liquid discharge. In an embodiment a discharge flow is provided that bends a liquid flow out of the inlet flow into the settling chamber. In an embodiment the flow towards the liquid discharge is directed upwards.

In an embodiment the gas separation device forming the inlet of the settling chamber is arranged to have a capacity of approximately 1.5-4×times the liquid discharge outflow of the settling device.

In an embodiment the gas separation device, and preferably the oblique plates are constructed and arranged to obtain a semi-laminar flow of the fluid entering the settling chamber. Such a semi-laminar flow is preferred since it is free of disturbances, and subsequent separation steps can be performed without much disturbance.

In an embodiment the oblique plates of the gas separation device are arranged to cause a generally downward flow into the settling chamber. In an embodiment the particulate material separation device is arranged to cause a flow in a generally upward direction from the settling chamber to the liquid discharge.

In an embodiment at the transition between gas separation device and settling chamber a downwardly directed baffle is provided. The baffle can direct the flow in a generally vertical downward direction.

In an embodiment particulate separation device is positioned downstream from the settling chamber and upstream from the liquid discharge.

In an embodiment the gas separation device and particulate separation device are positioned adjacently with respect to the settling chamber. In an embodiment the inlet flow into the settling chamber and the outlet flow out of the setting chamber are positioned adjacently. Both separation devices are connected to the settling chamber. A discharge flow towards the liquid discharge will reach the discharge (effluent) only after passing the particulate material separation device. Even though a skilled person will be reluctant to position the flows opposite one another, it was found that in general the disturbances in the flow in the settling chamber remain very low and that in fact the separating efficiency in the settling chamber was increased.

An exit of the gas separation device is preferably directed away from an inlet direction of the particulate separation device. In an embodiment the liquid discharge device are positioned downstream from the particulate separation device, and liquid to be discharged will need to end out of the exit flow from the gas separation device in order to reach the liquid discharge.

In an advantageous embodiment the exit flow from the gas separation device is directed downward, while a liquid flow is obtained by bending out the liquid from said downward flow. This will increase the separation efficiency of the settling chamber by inducing little or no disturbances.

In an embodiment the settling chamber comprises an outlet for fluid and particulate material, said outlet in an embodiment forming a slit or longitudinal opening, and in an embodiment comprising a variable slit for controlling the outflow.

In an embodiment the particulate separation device and gas discharge device comprise oblique plates. In an embodiment oblique parallel plates form the gas separation device and particulate separation device separated by a separation plate. Such a construction is cost effective.

According to an aspect of the invention a purifier is provided for example the aerobic or anaerobic purification of waste water. In an embodiment the purifier comprises a process tank having a reaction chamber such as a fermentation chamber. In an embodiment a settling device is part of the purifier. The settling device can be fitted inside the purifier or placed externally. In an embodiment the settling device is manufactured separately. In an embodiment the settling device comprises a combination of features of the settling device described above. The settling device has an inlet near the fluid level of the tank. Positioning the settler inlet close to the fluid level will result in generally almost complete degassing of the fluid before entering the settling device, resulting in a low gas inflow of the settling device.

In an embodiment the purifier according to the invention comprises a degassing compartment. The degassing compartment is preferably situated next to or adjacent a settling device. In an embodiment a gas-rich, first compartment is linked to the process (e.g. fermentation) chamber.

In a further embodiment gas trapping devices are fitted between the fermentation chamber and the inlet of settling device chamber of the settling device. The gas trapping devices trap gas bubbles rising in the fermentation chamber.

At the top, near the fluid level, of a degassing chamber, gas is able to escape from the fluid. The escaped gas can then be discharged, after which a fluid remains which is poorer in gas. The fluid, which is poorer in gas, is subsequently conducted onward via the inlet of the settling device so as to reach the settling chamber. Since in an embodiment the fluid undergoes a downward motion through the gas separation device formed by oblique plates in an overlapping arrangement, a portion of the gas bubbles can flow back in the opposite direction so as to escape from the fluid at the top of the degassing chamber and be able to be discharged. Particles settled in the settling chamber and in the degassing compartment will be returned to the process chamber assisted by the flow through a sludge outlet of the settling device near a bottom of the settling chamber connected to that process chamber.

Using such a purifier, waste water such as waste water from for example breweries or from food industry, or suspended solids-containing waste water, can be very well cleaned.

In an embodiment wastewater is pumped from a pump pit to the reactor. Before entering the reactor the wastewater can be mixed with recirculation water from the reactor. This recirculation can provide sufficient mixing inside the reactor. In the mixed stream of wastewater and circulation water (reactor feed flow) nutrients and caustic can be dosed.

In an embodiment produced biogas rises to the top of the reactor and is released from the water phase into a headspace of the reactor. Preferably water and sludge flow into the gas separator of the settling device or 3-phase separator according to the invention. The rising biogas in the reactor creates a so-called gas lift. Therefore more water is flowing into the inlet of the settling device than the actual effluent flow that is leaving the reactor/settling chamber through the liquid discharge. This results in a circulation over the gas separator.

The reactor effluent flows up in the particulate material separator, in an embodiment formed by oblique overlapping plates, where fine suspended material is separated from the water. Liquid is discharged as effluent flowing via the overflow weirs into the central effluent gutter. From this gutter the effluent leaves the reactor via e.g. an internal standpipe (water lock), to prevent that biogas escapes via the effluent pipe.

By using plate separators in the settling device a large settling surface is created (projected surface), which results in a better separation Besides sludge removal the treated wastewater is also partially degassed in the 3-phase separator.

In order to provide sufficient mixing in the reactor, in an embodiment fluid is circulated over the reactor by a low shear pump. This circulation fluid is, in an embodiment, taken from a perforated ring, which is located beneath 3 phase separator/settling device according to the invention. Therefore the recirculation flow does not influence the up flow in the 3-phase separator.

The invention further relates to a method for the anaerobic or aerobic purification of waste water using a device according to the invention.

According to a further aspect of the invention a method for aerobic or anaerobic purification of a fluid of waste water is provided using a settling device having a settling chamber for containing the fluid wherein a flow of the fluid containing liquid gas and particulate material is provided through the settling chamber. In an embodiment the flow is provided by density differences in the fluid. In an embodiment of the method the gas and particulate material are separated from the fluid in the settling device. The fluid is discharged after sufficient purification as effluent. In an embodiment the flow comprises a laminar flow. Preferably the laminar flow is provided as fluid flow into the settling chamber. The laminar flow is a stable flow lacking disturbing turbulences, which could disturb the settling properties of a settling device.

The laminar flow is preferably directed vertically. Preferably the particulate material is passed along the laminar flow towards an exit of the settling chamber back into the fermentation chamber. In an embodiment a discharging flow, preferably a flow for discharging liquid is directed out of the laminar flow. Preferably the inflow of fluid into the settling chamber is pre-separated, e.g. the liquid and solid phases have already been separated partially.

Preferably a liquid discharge flow is directed out of the inflow into the settling chamber. Preferably the inlet flow is directed in a generally opposite direction away from the discharge outlet. Contrary to the knowledge of the skilled man, such an opposite/perpendicular directed flow causes little disturbances, especially if already a first step of separation is achieved between liquid and sludge phase, but the separation efficiency is improved.

According to a further aspect a method of aerobic or anaerobic purification of a fluid of waste water is provided using a settling device having a settling chamber for containing the fluid wherein a flow of the fluid containing liquid gas and particulate material is provided through the settling chamber. Gas and particulate material are separated from the fluid in a settling device. The liquid is discharged as effluent. A flow of fluid is provided into and out of the settling device through a settling chamber. The fluid flows into the settling device near a liquid level of the fluid. The method according to the invention is characterized in that the gas is separated from the fluid during supply of the fluid into the settling chamber. Separation of gas is part of the settling device, and active separation of gas from the fluid is a first step of the settling device preventing gas from penetrating into the settling chamber and causing disturbances there.

Although the invention will be described here referring to specific embodiments, it will be clear to the skilled reader that the invention is not limited to these specific embodiments. The invention encompasses any combination of the inventive features according to the invention comprising any of the explicit or implicit features as disclosed herein. The disclosure of the application is not limited to the combination of features according to the appended claims and could be directed at any of the explicit or implicit features as disclosed herein.

The invention will be explained in greater detail below with reference to the appended drawing. A purifier according to the invention is illustrated by way of example in this drawing, in which.

Figure 1:
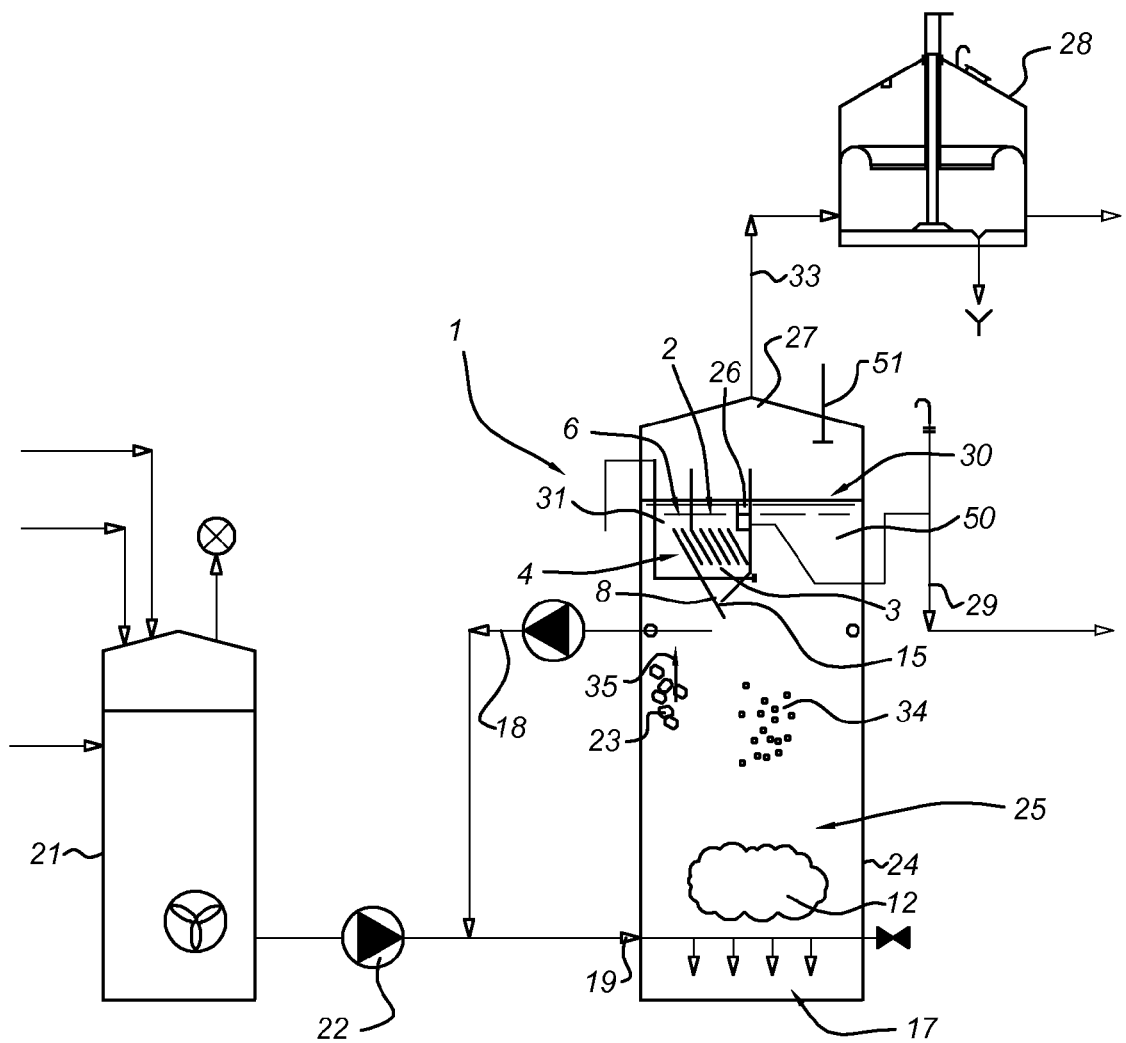
FIG. 1 is a schematic view of a wastewater treatment device according to an embodiment of the invention.

FIG. 1 shows a cleaning device 1, herein also referred to as a reactor or digester. Preferably digester 1 is a UASB reactor, however the applications of the invention are not limited to UASB reactors and can relate to EGSB, aerobic reactors or similar types of reactors. The cleaning device 1 could be used as a wastewater treatment. The cleaning device 1 is capable of performing a process of removing contaminants from wastewater. It includes physical, chemical and biological processes to remove physical, chemical and biological contaminants. Its objective is to produce a waste stream (or treated effluent) and a solid waste or sludge suitable for discharge or reuse back into the environment. The cleaning device can be used in industrial plants to treat the sewage liquor using anaerobic or aerobic biological processes.

In order to use less space, treat difficult waste, deal with intermittent flow or achieve higher environmental standards, a number of designs of hybrid treatment plants have been produced. Such plants often combine all or at least two stages of the three main treatment stages into one combined stage.

The present invention is in the area of anaerobic waste water purification and more in particular anaerobic sludge bed systems, such as Upflow Anaerobic Sludge Blanket (UASB) systems.

The reactor 1 is provided with a three phase separator or settling device 2 according to the invention. In this specific embodiment a settling device 2 is provided for an upflow anaerobic sludge blanket reactor. However, the settling device 2 according to the invention is not limited to applications in UASB-reactors.

The cleaning device 1 further comprises a process chamber 25, such as a fermentation chamber, above which there is fitted the settling device 2.

The cleaning device 1 further comprises a degassing chamber 50. At the top of the degassing chamber 50 there is provided a gas discharge 27 and in an embodiment a spray device 51 for spraying water with the aim of releasing gas bubbles attached to floating particles from said particles. At the top of the degassing chamber 50, at the water level 30, a discharge (not represented) for floating particles can be provided.

UASB uses an anaerobic process whilst forming a blanket 12 of granular sludge 23 which suspends in the tank 24. In order to form such a blanket 12, in the specific embodiment as shown in FIG. 1, wastewater flows from the influent tank 21 via a centrifugal pump 22 into the tank 24 through supply 19 and consequently into the tank 24 of the UASB reactor with the settling device 2.

In an embodiment a recirculation arrangement 18 is fitted in the process chamber 25. The recirculation arrangement allows further mixing of the fluid present in the reactor. The recirculation can use the same supply 19 as the influent tank 21 to re-enter the process chamber 25.

In the shown embodiment wastewater flows upwards through the blanket 12 and organic material is processed (degraded) by the (an-)aerobic microorganisms. The upward flow mixes with and suspends the blanket 12. The solids retention time differs from the hydraulic retention time enabling the degradation of these solids.

As mentioned earlier, the anaerobic purification equipment shown in FIG. 1 comprises a tall container or tank 24. At the bottom end of the cleaning device 1, there is provided a mixing zone 17 for influent introduced via supply 19. The mixing zone 17 can be accomplished in several ways. One advantageous manner of accomplishing the mixing zone is providing an inlet system in accordance with WO 92/01637, incorporated by reference.

In the upper part of the reactor tank 24, an effluent outlet, for instance water-collecting means in the form of overflow gutters 26 or other means are fitted which are connected to an effluent pipe 29 for discharging purified effluent. The water-collecting means are located at the level of the liquid surface 30 in the reactor tank 24.

The process or fermentation chamber 25 and the settling device 2 could be separated from each other by means of separating caps (not shown), as known from EP-A1-0,244,029 and EP-A1-0,193,999 (both herein incorporated by reference). In an embodiment the reactor tank 24 is fitted with a gas collecting arrangement for collecting and removing gas (not shown). The gas collecting arrangement can comprise a multiplicity of hoods/caps. Per gas collecting arrangement the hoods can be arranged in one layer or several layers, such as three layers. The reactor is gas-proof closed at the top.

In operation gas bubbles 34 are produced, flowing upwards 35, which set the fluid in the settling device 2 into violent motion, whereupon sludge particles 23 and other particles swirl through the fluid. At the top of the tank 24, gas is able to escape from the fluid. The escaped gas can then be discharged, after which a fluid remains which is poorer in gas.

The fluid 35 now poorer in gas, is subsequently conducted onward. A part of the fluid will return towards the bottom of tank 24.

Part of the fluid 35 can enter the settling device 2 and reach the bottom of the settling chamber 3 of the settling device 2. The flow into the settling device 2 is the result of sludge density differences in the reactor/settling chamber. As the gas is released near the surface 30, it will have a lower density.

During the downward motion through gas separation device 4 forming the inlet 6 of settling device 2 to enter settling chamber 3, a remaining portion of the gas bubbles which are still being transported can flow back in the opposite direction so as to escape from the fluid at the top of the degassing chamber 31 and is discharged. The fluid is subsequently conducted via the settling compartment 3. Particles present in the fluid are able to be deposited from the fluid. The deposited particles fall towards the bottom of the settling chamber 3 and make their way along the sludge outlet 8 formed by a slit 15 back into the process chamber 25.

In an embodiment, gas is formed in the settling chamber. In the setting chamber, despite the fact that the disturbing turbulence from the gas should be absent, it is still possible for the gas to escape.

The task of the settling device 2 is to separate the liquid from gas and sludge. The liquid can leave the cleaning device 1 through a liquid discharge in the form of the effluent outlet 26. The gas is collected at the gas discharge or gas outlet 27 from where the gas can reach a gas collection system 28. Gas collector system 28 may be formed by a gas buffer connected by conduit 33 with the gas discharge 27.

Figure 2:
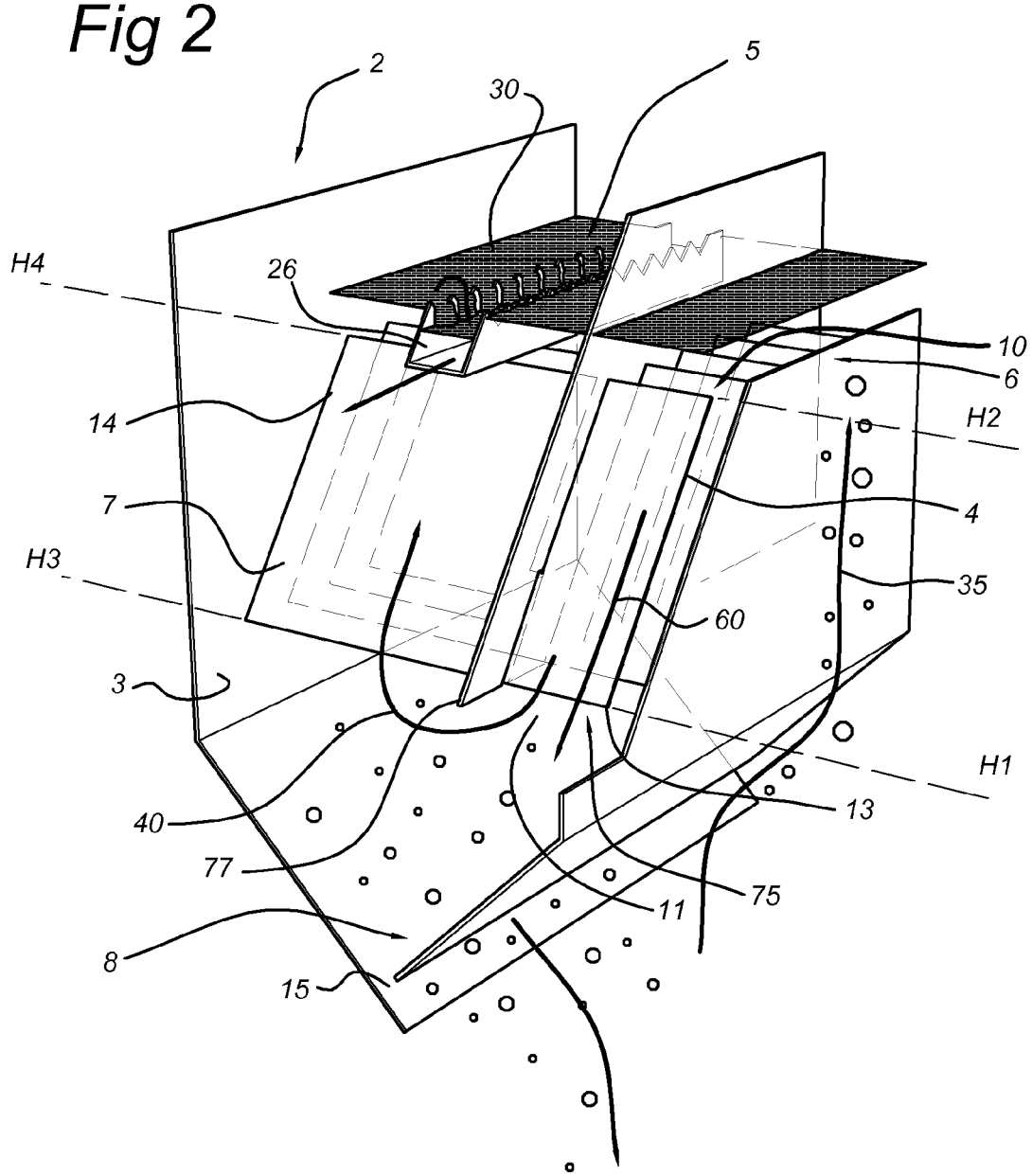
FIG. 2 shows an embodiment of the settling device according to the invention.

In a preferred embodiment shown in FIG. 2, the settling device 2 comprises a settling chamber 3. In the settling chamber 3 at least a part of the liquid fraction and particulate material fraction are generally separated. Before reaching the settling chamber 3 the fluid should enter the settling device 2 through inlet 6 and will have to pass gas separation device 4 wherein gas is actively separated from the liquid and sludge. The inlet to the settling chamber 3 may be formed by the gas separation device 4.

The settling device 2 according to the embodiment of FIG. 2 comprises a liquid-discharge device 5 for discharging liquid from the settling chamber 3 fitted close to the liquid level 30. In a preferred embodiment the effluent outlet 26 is used. The amount of liquid discharged can be controlled by influent pump 22.

The cleaned liquid can reach effluent outlet 26, more specifically the gutter 26 after passing through the settling chamber 3 and particulate material separation device 7, for instance following fluid flow arrows 10 and 40. The gutter 26 and particulate material separation device 7 together form the liquid discharge device 5 according to an embodiment of the invention. The liquid discharge device 5 is that part of the settling device 2 that is connected to the settling chamber 3 and that is arranged and constructed to eventually obtain the cleaned liquid.

In the specific embodiment as shown in FIG. 2 the settling device 2 comprises gas separation device 4 having channels 9 formed between oblique plates 13. The inlet 6 of the separator device 4 is positioned close to the fluid level 30 and an outlet 11 thereof is positioned at the transition 75 into the settling chamber 3 at a lower level (H1). The plates 13 are positioned in an overlapping arrangement. The gas separation device 4 as a whole forms the fluid inlet of the settling chamber 3.

The materials to be used for these plates 13 can be the standard materials, such as steel, coated steel, plastics such as polypropylene, fiber reinforced plastics (epoxy and/or unsaturated polyester resins) and the like.

Figure 5:
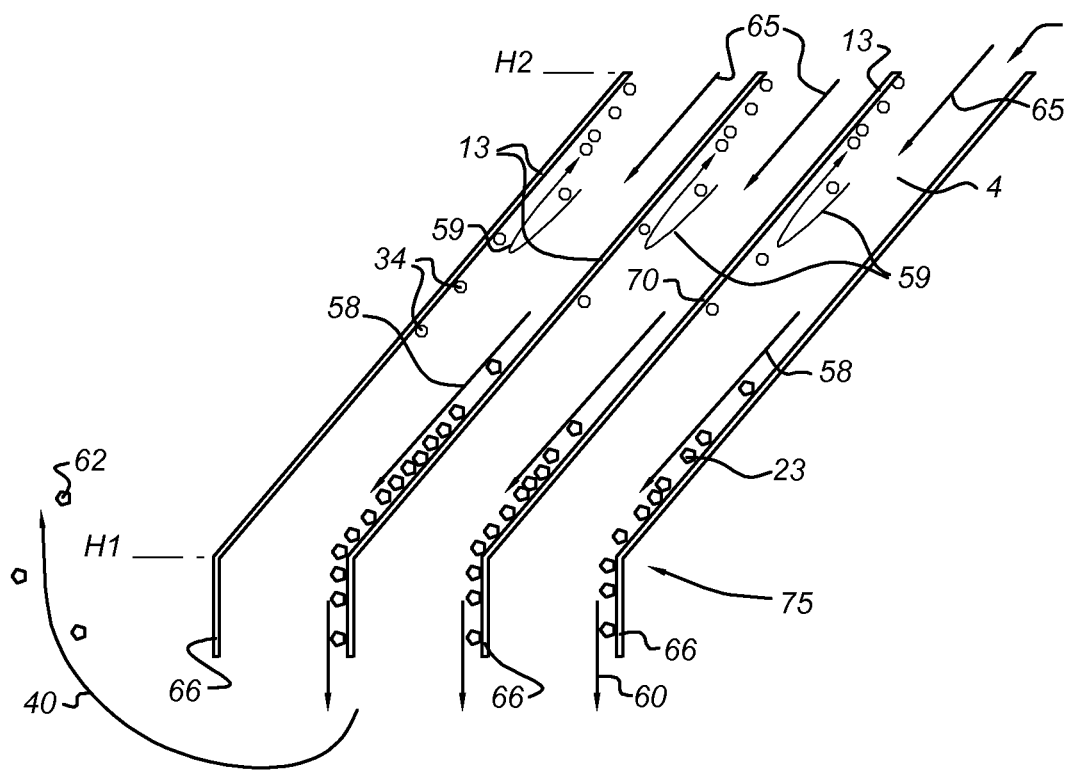
FIG. 5 shows a side view of a cross section of gas separation device according to an embodiment of the invention.

FIG. 5 shows a cross-sectional view of plates 13. During the downward flow of the fluid along the obliquely fitted plates 13, a semi-laminar flow will be formed in which heavier particles still present in the fluid will be easily deposited on an upper side 70. Near the transition 75 of plates 13 into settling chamber 3 the inflow of fluid will continue its flow motion into the settling chamber. Gas bubbles 34 and lighter, floatable particles will rise vertically, or in any event more steeply than the fluid itself, as a result of the upward lifting force which is thereby encountered. These bubbles and lighter particles are then forced into contact with an oblique face of an underside of a plate 13 and the lifting force will make these gaseous fragments and lighter particles rise in an opposite direction 59 with respect to the sinking fluid 58. The gas and the lighter particles will exit the gas separation device at the inlet 6.

The sludge particles 23 which are present in the fluid flow 65 in the gas separation device 4 are able to settle on the surface area 70 of the plates 13. Sludge particles 23 are dragged 58 downwards with the flow 60 between plates 13 from level H2 to H1. The gas separation device 4, or more generally the inlet 6 of the settling chamber 3, is arranged and constructed to partially allow flocculation in case of flocculent sludge 23 and to eventually create a fluid flow into the settling chamber wherein the fluid contains a flow of particles 23.

In a specific embodiment, the (device forming the) inlet 6 (of settling chamber 3) comprises at least two or more separation devices, for example at least three oblique overlapping plates 13, tubes, pipes etc. to further pre-separate the fluid flow 65, comprising sludge-fluid compartments, into at least two or more generally laminar (adjacent according to FIG. 5) fluid flows 65.

The fluid flow reaching the settling chamber 3 will have a semi-laminar arrangement or inflow pattern, as is most clear from FIG. 5. A liquid portion 62 is surrounded by two sludge portions 23. At the transition 75 of plates 13 into the settling chamber 3 the liquid and sludge fraction are at least partially separated according to the method shown in FIGS. 2 and 5.

At the end of plates 13 near the transition 75 into the settling chamber 3, plates 13 can be provided with a baffle 66. Baffle 66 in this embodiment is positioned vertically (downwards) and is functioning as a guidance for the flow of the fluid into the settling chamber 3, guiding the flow in a generally vertically directed flow pattern. This vertical flow pattern is less disturbing for the pre-settled heavy sludge particles under the force of gravity because the displacement direction is identical. The vertically downward flow pattern can continue in the generally pre-separated form as it leaves the plate arrangement 4.

The gas separation device 4 according to an embodiment comprises a row of oblique parallel plates 13 fitted at mutual horizontal intervals of 2 to 18 cm, preferably 13 cm. In an embodiment the separation device 4 comprises channels. The channels have an inlet 6 near water level 30, H2. The outlet of the tubes near H1 can comprise a hook/baffle 66 for guiding the fluid/sludge liquid in a vertical flow pattern.

As mentioned earlier, the settling chamber 3 comprises a sludge outlet 8, preferably fitted near a bottom of the settling chamber 3. In the present embodiment the sludge outlet 8 is formed by a slit 15, preferably a variable slit 15, for effecting the fluid flow and to enable settled sludge to return to the reactor 25 (as seen in FIG. 1). Specific embodiments are described in more detail with reference to FIGS. 3-4.

In a preferred embodiment the cleaning device 1 comprises a settling device 2, wherein a position of the outlet means 8 can be arranged at least in and out of the flow pattern of fluid or displacement direction of the flow entering the settling chamber 3. This will allow control of the disturbance of the fluid patterns in the settling chamber. If the outlet means 8 is positioned in a direct line of the inlet flow pattern, the inlet flow can leave the setting chamber without causing much disturbance in the settling chamber 3.

In an embodiment the liquid discharge 5 is arranged to create an outflow out of the inflow pattern of fluid entering the settling chamber. Preferably the liquid discharge device and in particular the entry towards the discharge is arranged and constructed to further separate the pre-separated flow pattern of fluid entering the settling chamber, wherein the liquid discharge device provides a force sufficient to bend 40 part of a liquid portion out of the inflow pattern. Since liquid can leave the settling chamber 3 via the liquid discharge as effluent, part of the inflow into the settling chamber will not be returned through the sludge outlet back to the reactor. The kinetic energy of the flow through the inlet and out the sludge outlet is considerably higher than the kinetic energy of the flow towards the liquid-discharge.

The settling chamber is of suitable size to allow the further separation of the pre-separated inflow pattern of fluid into the settling chamber. In an embodiment the vertical flow pattern comprises a pattern of sludge and liquid in a first direction, while a liquid discharge device 5 is provided adjacent said pattern, adjacent in a second direction. This is in conformity with the embodiment shown in FIG. 2.

In an embodiment the inlet flow pattern is provided in a middle part of a settling chamber, wherein liquid discharge device are provided on both side of the flow pattern to allow bending out the liquid fragment on both side of the pre-separated flow pattern. This will further increase the efficiency of the settling device 2.

As part of the liquid discharge, a particulate material separation device 7 is positioned downstream from the settling chamber 3 and upstream from the effluent gutter 26, which is arranged and constructed to actively separate particles from the fluid 40. In the embodiment according to FIG. 3-4 the particulate material separation device extends over an height difference of H3 to H4.

In a specific embodiment the particulate material separation device 7 comprise a likewise structure (plates/tubes/pipes etc.) as the gas separation device 4. Such a construction, now having an upwardly directed flow, will allow separation of the particulate material present in the fluid. During the upward flowing of the fluid along the bottom of the obliquely fitted plates 14, a semi-laminar flow will be formed in which heavier particles still present in the fluid will be easily deposited and flow in a reverse direction.

Figure 3:
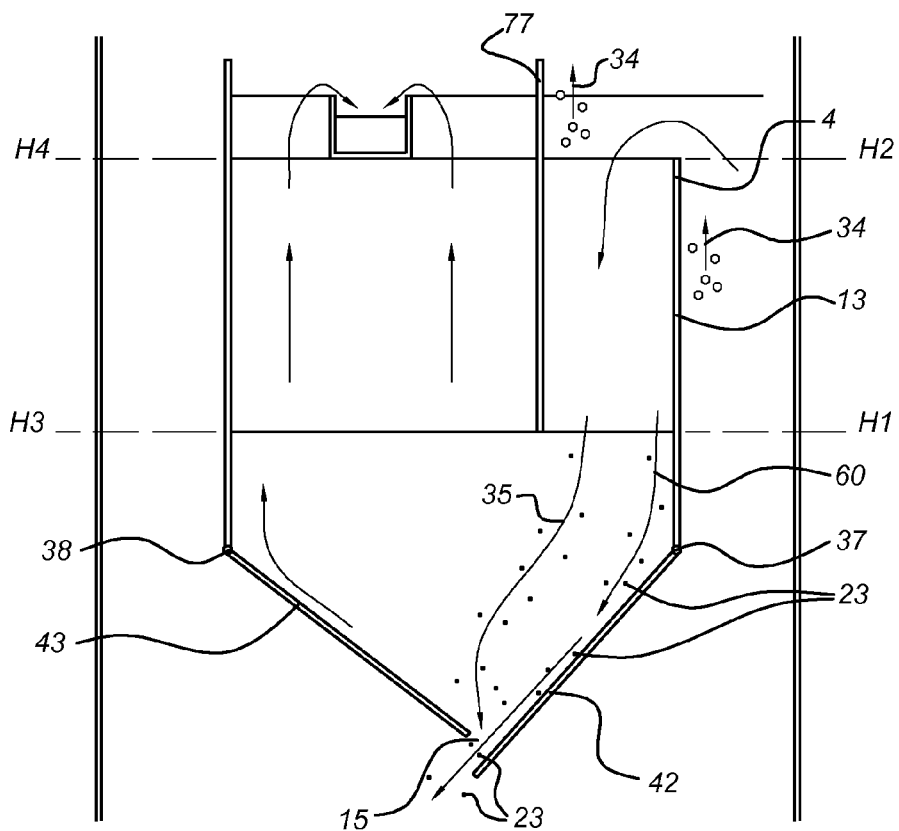
FIGS. 3-4 show front views of a cross section of a settling device according to the invention.
Figure 4:
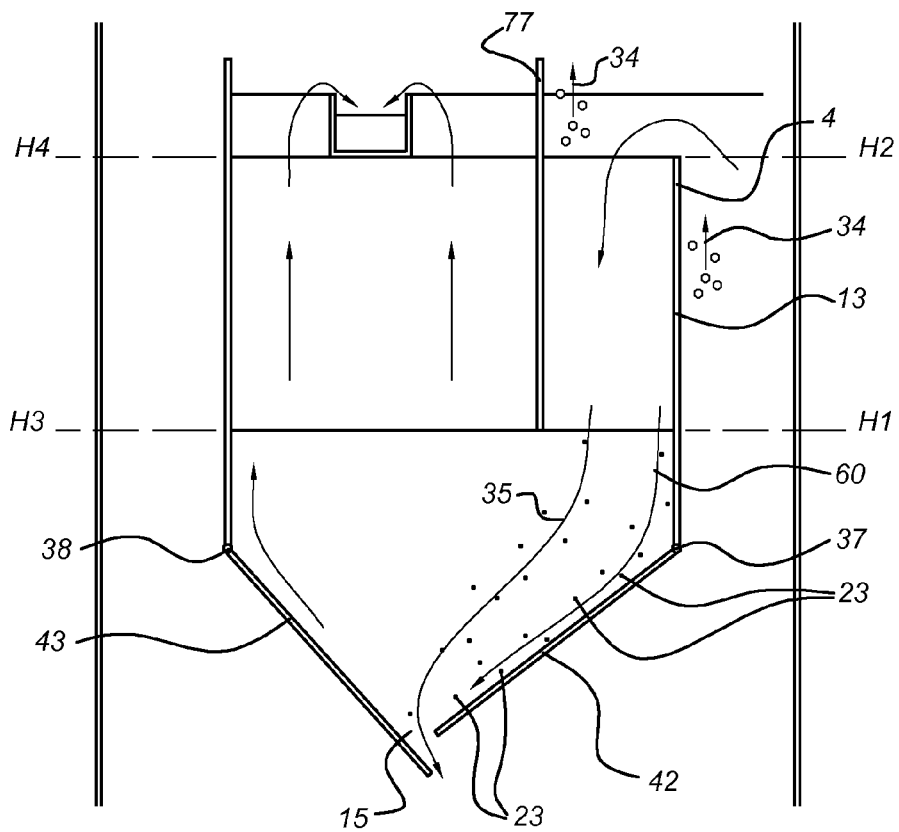

In the specific embodiment according to FIG. 2 gas separation device 4 and particulate material separation device 7 comprise the same plates 13/14. The gas separation device 4 and particulate material separation device 7 are separated by a separation plate 77. The separation plate 77 in this embodiment can be used to set a ratio of between the separation device 4,7. In this specific embodiment, as shown in FIGS. 2-4, the ratio is 2:1 (particulate separation:gas separation).

The particles 23 entering the settling chamber 3 will for the most part remain in the vertically directed flow part and will flow through the settling chamber 3 in the direction of the sludge outlet 8 formed by outlet 15.

The settling chamber 3 comprises a partially V-shaped house. In the specific embodiment according to FIG. 2, an upward end of the settling chamber comprises the gas/particulate material separation device 4,7. Other sides of the settling chamber comprises vertical walls, and two sloping walls 42 and 43. In the specific embodiment according to FIG. 2 settling chamber 3 has a V-shaped downwardly projection outlet 15.

Walls 42 and 43 are hinged, but can be fixed in a position, via a frame joint 37/38. Control of the position of walls 42,43 allows control of the size and position of the slit 15. The settling device 2 can comprise an actuator to control the position of the walls 42,43.

By moving one and or both walls 42,43 over joints 37/38 fluid flow 62 can be affected. FIGS. 3-4 show three different positions of the walls 42/43. The position of slit is controlled to correspond with the intensity of gas formation in the reactor 25 combined with the depth of the settling chamber.

FIG. 3 shows a position of walls 42/43 in operation during a start up or in a situation of low gas formation. Outlet 15 is positioned more or less in the path of the inlet flow into the settling chamber. Such a position is beneficial if the gas formation is low. The opening 15 is positioned in order not to form a restriction of the gas flow in and out of the settling device 2.

FIG. 4 shows a different state of the settling device 2 for a medium gas strain. Now an outward flow needs to make a 'turn' in order to flow out of the slit 15. This will restrict the flow.

Within the scope of the invention various modifications are possible. The embodiments drawn and described are only examples. All embodiments have in common that a significant portion, close to 100%, of the gas is not allowed to enter the settling chamber. The load capacity of the settling device is considerably increased as a result of the tranquility due to earlier and additional gas separation. Further a semi-laminar flow is obtained in the settling chamber.

The invention claimed is:

1. Settling device (2) for a fluid containing liquid, gas and particulate material, comprising:
   a settling chamber (3) configured to be filled with the fluid;
   a liquid-discharge (5) configured to discharge liquid from the settling chamber, the liquid discharge (5) being arranged so as to be at the liquid level (30) when in operation;
   a fluid inlet (6) configured to supply the fluid into the settling chamber (3) and arranged at essentially the same level as the liquid-discharge (5);
   a particulate material separation device (7) positioned between the settling chamber (3) and the liquid discharge (5); and
   a sludge outlet (8) from the settling chamber (3)
   wherein the inlet (6) comprises a gas separation device (4) arranged to separate gas from the fluid, the gas separation device (4) comprising a row of oblique plates (13) extending below the level where fluid is introduced in the gas separation device, the plates (13) being disposed in overlapping and parallel arrangement with their longitudinal axes at an angle to the horizontal.

2. Settling device according to claim 1, wherein the gas separation device (4) comprises an inlet (6) at the fluid level (30, H1) and an outlet (75) positioned in the settling chamber (3) at a lower level (H2).

3. Settling device according to claim 2, wherein the oblique plates (13) of the inlet device (4) are arranged to create a semi-laminar flow of the fluid into the setting chamber (3).

4. Settling device according to claim 2, wherein the particulate material separation device (7) comprises a row of oblique parallel plates (14).

5. Settling device according to claim 1, wherein the oblique plates (13) of the inlet device (4) are arranged to create a semi-laminar flow of the fluid into the setting chamber (3).

6. Settling device according to claim 1, wherein the particulate material separation device (7) comprises a row of oblique parallel plates (14).

7. Settling device as claimed in claim 6, wherein the oblique parallel plates (13) of the gas separation device (4) and the oblique parallel plates (14) of the particulate material separation device (7) are constructed and arranged to cause a flow in the downward direction from the inlet (6) to the settling chamber (3) and a flow in the upward direction from the settling chamber (3) to the liquid discharge (5).

8. Settling device according to claim 6, wherein the particulate material separation device (7) and gas separation device (4) are separated by a separation plate (77).

9. Settling device according to claim 1, wherein the oblique parallel plates (13,14) have a length of 50 to 200 cm.

10. Settling device according to claim 1, wherein the gas separation device (4) and particulate material separation device (7) are adjacently positioned above and connected with the settling chamber (3).

11. Settling device according to claim 1, wherein the sludge outlet (8) is fitted near a bottom of the settling chamber (3) and is formed by a slit (15).

12. Settling device according claim 11, wherein the sludge outlet (8) can be positioned at least in and out of the flow path of fluid entering the settling chamber (3) through the inlet (4,6).

13. Settling device as claimed in claim 1, wherein the oblique plates of the gas separation device (4) extend downward from the inlet (6) to the gas separation device outlet (11) so that the exit liquid flow from the gas separation device (4) is directed downward.

14. Settling device as claimed in claim 1, wherein an oblique plate of the gas separation device (4) comprises a baffle (66) positioned vertically so as to guide the flow generally downward.

15. Purifier (1) for the aerobic or anaerobic purification of waste water, comprising:
    a reaction chamber (24) comprising a process chamber (25),
    a settling device (2) according to claim 1, which is fitted above the process chamber (25),
    a degassing compartment (50) connected to an inlet (4,6) of the settling device (2) positioned near the fluid level (30).

16. Purifier (1) of claim 15, wherein the process chamber (25) is a fermentation chamber.

17. Method for the aerobic or anaerobic purification of a fluid of waste water using a settling device (2) as claimed in claim 1, the method comprising:
    supplying the fluid supplied through the inlet (6) and causing the fluid to flow obliquely downward;
    causing gas bubbles (34) and/or light particles contained in the liquid to collect at an underside of a plate (13), to flow in an upward direction and to exit the gas separation device (4) from the inlet (6);
    causing the remainder of the fluid to continue flowing in a downward direction into the settling chamber (3).

18. Settling device according to claim 1, wherein the oblique parallel plates (13,14) have a length of 80 to 140 cm.

19. Method for the aerobic or anaerobic purification of a fluid of waste water using a settling device (2) having a settling chamber (3) for containing the fluid and a particulate material separation device (7) positioned between the settling chamber (3) and a liquid discharge (5),
    wherein a flow of a fluid containing liquid, gas and particulate material is provided into and out of the settling device (2) through the settling chamber (3),
    wherein gas and particulate material are separated from the fluid in the settling device (2),
    wherein liquid is discharged from the settling device (2) as effluent via the liquid discharge (5), the fluid flowing into the settling device (2) being provided near a liquid level of the fluid,
    wherein gas is separated from the fluid in the inlet, upstream from the settling chamber (3) by a row of oblique plates (13) extending below the level where fluid is introduced in the gas separation device, the plates (13) being disposed in overlapping and parallel arrangement with their longitudinal axes at an angle to the horizontal such that fluid supplied through the inlet (6) is caused to flow obliquely downward along the oblique plates (13).

20. Method according to claim 19, wherein the flow into the settling chamber (3) and a discharge flow out of the settling chamber (3) through the material separation device (7) towards the effluent discharge (26) are adjacent and generally oppositely directed.

* * * * *